United States Patent
Peter et al.

(10) Patent No.: US 10,835,127 B2
(45) Date of Patent: Nov. 17, 2020

(54) ATHEROSCLEROTIC PLAQUE DETECTION

(71) Applicant: BAKER IDI HEART & DIABETES INSTITUTE HOLDINGS LIMITED, Melbourne (AU)

(72) Inventors: Karlheinz Peter, Hawthorne (AU); Nay Min Htun, South Yara (AU); Yung-Chih Chen, Box Hill South (AU)

(73) Assignee: BAKER IDI HEART & DIABETES INSTITUTE HOLDINGS LIMITED, Melbourne (AU)

( * ) Notice: Subject to any disclaimer, the term of this patent is extended or adjusted under 35 U.S.C. 154(b) by 0 days.

(21) Appl. No.: 14/394,057

(22) PCT Filed: Apr. 12, 2013

(86) PCT No.: PCT/AU2013/000373
§ 371 (c)(1),
(2) Date: Oct. 10, 2014

(87) PCT Pub. No.: WO2013/152395
PCT Pub. Date: Oct. 17, 2013

(65) Prior Publication Data
US 2015/0080686 A1     Mar. 19, 2015

(30) Foreign Application Priority Data
Apr. 13, 2012   (AU) .............................. 2012901476

(51) Int. Cl.
*A61B 5/00* (2006.01)
*A61B 5/02* (2006.01)

(52) U.S. Cl.
CPC .......... *A61B 5/0086* (2013.01); *A61B 5/0071* (2013.01); *A61B 5/0084* (2013.01);
(Continued)

(58) Field of Classification Search
CPC ... A61B 5/0059; A61B 5/0075; A61B 5/0086; A61B 5/0091; A61B 5/0071;
(Continued)

(56) References Cited

U.S. PATENT DOCUMENTS 4,648,892 A * 3/1987 Kittrell ................. A61B 17/22
                                                         600/342
4,718,417 A * 1/1988 Kittrell .............. A61B 1/00183
                                                         600/317
(Continued)

FOREIGN PATENT DOCUMENTS

CA      1279901 C    2/1991
JP      61-257638 A  11/1986
(Continued)

OTHER PUBLICATIONS

Park, "Biochemical characterization of atherosclerotic plaques by endogenous multispectral fluorescence lifetime imaging microscopy", Atherosclerosis, 220(2), pp. 394-401 (Year: 2012).*
(Continued)

*Primary Examiner* — Joanne M Hoffman
(74) *Attorney, Agent, or Firm* — Knobbe, Martens, Olson & Bear, LLP

(57) ABSTRACT

An apparatus detects atherosclerotic plaques. The apparatus includes an electronic processing device that determines a level of fluorescence sensed by a sensor at a second infrared wavelength in response to exposure of at least part of an artery to radiation at a first infrared wavelength and determines a fluorescence indicator using the level of fluorescence. The fluorescence indicator is indicative of the presence, absence or degree of an atherosclerotic plaque.

11 Claims, 11 Drawing Sheets

(52) U.S. Cl.
CPC .......... *A61B 5/02007* (2013.01); *A61B 5/725* (2013.01); *A61B 5/7246* (2013.01); *A61B 5/7275* (2013.01); *A61B 5/7282* (2013.01); *A61B 2576/02* (2013.01)

(58) Field of Classification Search
CPC . A61B 5/0084; A61B 5/02007; A61B 5/7246; A61B 5/725; A61B 5/7275; A61B 5/7282; G01N 21/4795
See application file for complete search history.

(56) References Cited

U.S. PATENT DOCUMENTS

| | | | | |
|---|---|---|---|---|
| 4,785,806 A * | 11/1988 | Deckelbaum | .......... | A61B 18/20 606/15 |
| 4,981,138 A * | 1/1991 | Deckelbaum | ........ | A61B 5/0071 600/477 |
| 5,046,501 A * | 9/1991 | Crilly | .................. | A61B 5/0071 600/477 |
| 5,275,594 A * | 1/1994 | Baker | .................. | A61B 18/245 606/12 |
| 5,507,287 A * | 4/1996 | Palcic | ................ | A61B 1/00186 356/318 |
| 5,590,660 A * | 1/1997 | MacAulay | ............. | A61B 1/043 600/160 |
| 6,095,982 A * | 8/2000 | Richards-Kortum | ........................ | A61B 5/0071 356/301 |
| 6,186,780 B1 | 2/2001 | Hibst | | |
| 6,258,576 B1 * | 7/2001 | Richards-Kortum | ........................ | A61B 5/0059 425/288 |
| 6,485,300 B1 * | 11/2002 | Muller | ............... | A46B 15/0002 433/29 |
| 6,913,743 B2 * | 7/2005 | Licha | ................. | A61K 49/0017 424/1.11 |
| 7,603,166 B2 * | 10/2009 | Casscells et al. | ............. | 600/473 |
| 7,865,231 B2 * | 1/2011 | Tearney et al. | ............... | 600/476 |
| 2003/0044353 A1 | 3/2003 | Weissleder | ........... | C12Q 1/6816 424/9.6 |
| 2003/0055307 A1 * | 3/2003 | Elmaleh | ............... | A61B 5/0071 600/1 |
| 2004/0186383 A1 * | 9/2004 | Rava | .................... | A61B 5/0071 600/473 |
| 2004/0243022 A1 * | 12/2004 | Carney | ................ | A61B 5/0086 600/552 |
| 2005/0260677 A1 * | 11/2005 | Saaski | .................. | G01N 21/553 435/7.1 |
| 2006/0041199 A1 * | 2/2006 | Elmaleh | ............... | A61B 5/0071 600/478 |
| 2007/0073162 A1 * | 3/2007 | Tearney | ............. | A61B 1/00082 600/476 |
| 2007/0078348 A1 * | 4/2007 | Holman | ............... | A61B 5/0075 600/473 |
| 2007/0167836 A1 * | 7/2007 | Scepanovic et al. | ......... | 600/476 |
| 2008/0058587 A1 | 3/2008 | Boyden | | |
| 2008/0103355 A1 * | 5/2008 | Boyden | ................ | A61B 5/0071 600/103 |
| 2008/0129993 A1 | 6/2008 | Brennan et al. | | |
| 2008/0193376 A1 * | 8/2008 | Tawakol | ............ | A61K 41/0057 424/1.61 |
| 2008/0221457 A1 * | 9/2008 | Zeng | ................... | A61B 5/0071 600/477 |
| 2009/0036770 A1 | 2/2009 | Tearney et al. | | |
| 2009/0073439 A1 | 3/2009 | Tearney et al. | | |
| 2009/0192358 A1 * | 7/2009 | Jaffer | ................... | A61B 5/0066 600/182 |
| 2009/0231578 A1 | 9/2009 | Ling et al. | | |
| 2010/0272651 A1 * | 10/2010 | Georgakoudi | ..... | A61K 49/0047 424/9.6 |
| 2010/0315632 A1 * | 12/2010 | Brennan, III | ................. | 356/301 |
| 2011/0275899 A1 | 11/2011 | Tearney et al. | | |
| 2012/0022338 A1 | 1/2012 | Subramaniam et al. | | |

FOREIGN PATENT DOCUMENTS

| | | |
|---|---|---|
| JP | 2013-505468 A | 2/2013 |
| WO | WO 2005/052558 A1 | 6/2005 |
| WO | WO 2009/029216 A1 | 3/2009 |
| WO | WO 2011/038006 A1 | 3/2011 |

OTHER PUBLICATIONS

Marcu, "Detection of rupture-prone atherosclerotic plaques by time-resolved laser-induced fluorescence spectroscopy", Atherosclerosis, 204, pp. 156-164 (Year: 2009).*
Gillenwater, "Noninvasice Diagnosis of Oral Neoplasia Based on Fluorescence Spectroscopy and Native Tissue Autofluroescence", JAMA Otolaryngology—Head and Neck Surgery, 124(11) pp. 1251-1258 (Year: 1998).*
Fang, "Diagnosis of Vulnerable Atherosclerotic Plaques by Time-Resolved Fluorescence Spectroscopy and Ultrasound Imaging", IEEE (Year: 2006).*
International Search Report issued in PCT/AU2013/000373 dated Jun. 11, 2013.
Japanese Office Action, dated Jan. 30, 2017, in Japanese Patent Application No. 2015-504818 (with English translation).
Calfon, M.A., et al, In vivo Near Infrared Fluorescence (NIRF) Intravascular Molecular Imaging of Inflammatory Plaque, a Multimodal Approach to Imaging of Atherosclerosis, Journal of Visualized Experiments, 54, e2257, Aug. 2011.
Weissleder, R., et al, In vivo imaging of tumors with protease-activated near-infrared fluorescent probes, Nature Biotechnology, vol. 17, pp. 375-378, Apr. 1999.
Piotrowski et al., Evidence for Lipid Peroxidation in Atherosclerosis, Life Sciences, vol. 46, pp. 715-721, 1990.
Piotrowski et al., Mature Human Atherosclerotic Plaque Contains Peroxidized Phosphatidylcholine as a Major Lipid Peroxide, Life Sciences, vol. 58, No. 9, pp. 735-740, 1996.
Zhu et al., Development of a Near Infrared Fluorescence Catheter: Operating Characteristics and Feasibility for Atherosclerotic Plaque Detection, Journal of Physics D: Applied Physics, vol. 38, pp. 2701-2707, 2005.

* cited by examiner

ATHEROSCLEROTIC PLAQUE DETECTION

RELATED APPLICATIONS

This application is a U.S. National Phase of International Application No. PCT/AU2013/000373, filed Apr. 12, 2013, designating the U.S., and published as WO 2013/152395 on Oct. 17, 2013, which claims the benefit of Australian Patent Application No. 2012901476, filed Apr. 13, 2012.

BACKGROUND

The present invention relates to a method and apparatus for use in detecting atherosclerotic plaques using fluorescence spectroscopy, and in one example to detecting and/or quantifying the vulnerability of atherosclerotic plaques.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Atherosclerosis is currently a leading cause of mortality and morbidity worldwide. Atherosclerotic plaques can affect different arteries at different sites of the body, potentially leading to a multitude of clinical presentations. These lesions can be totally asymptomatic for years, can present with stable symptoms like exertional angina, or can suddenly lead to life-threatening complications such as myocardial infarction or stroke.

Fatty streaks composed of foam cells (lipid-filled macrophages) are the earliest lesions in atherosclerosis. These fatty streaks are harmless and fully reversible. Only some of these progress to more advanced stages of atherosclerosis. More advanced plaques become irreversible and contain varying proportions of cells (including smooth muscle cells, macrophages and T-cells), extracellular matrix (including collagen, elastin and proteoglycans) and lipids (intracellular and extracellular). Different morphological types of plaques emerge depending on their composition. Some are fibrous plaques consisting of fibrous tissues and calcifications without lipid-rich core and some become fibroatheroma with lipid-rich core covered by a thin fibrous cap.

Atherosclerosis is widely regarded as an inflammatory disease. Inflammatory cells play a key role not only in the pathogenesis of plaque progression but also in destabilising the plaque (inflammatory cytokines and proteolytic enzymes cause the disruption of the fibrous cap leading to plaque rupture and complications).

The development of atherosclerotic plaques is quite diverse. Some plaques remain quiescent for years and some become complicated leading to plaque rupture or erosions. Complicated plaques are the cause of thrombosis and occlusion of the arteries leading to potentially catastrophic outcomes. Plaque rupture is the commonest cause of coronary thrombosis.

The plaques which are prone to rapid progression and thrombosis or rupture, commonly known as rupture prone, are called "high risk/vulnerable plaques". Thin-cap fibroatheroma (TCFA), which is the hallmark of vulnerable plaque is described to have a few classical morphological features, namely a thin fibrous cap of <65 µm, a large necrotic core, increased plaque inflammation, positive vascular remodelling, increased vasa-vasorum neovascularisation and intraplaque haemorrhage.

However, despite extensive advances in the field of cardiovascular medicine, the ability for early detection of the complication-prone plaques (high risk/vulnerable plaques) before they rupture, remains elusive.

Several invasive plaque imaging techniques are being developed to detect TCFA. These methods are far from ideal at the current state and could detect only some, not all, features of vulnerable plaques. For example, IVUS (intravascular ultrasound) is able to detect positive remodelling but with its resolution of 100 to 250 µm, it is impossible to detect fibrous cap thickness or plaque inflammation. IVUS-VH (Virtual Histology) uses IVUS backscatter radiofrequency signal to detect the composition of the plaque, especially necrotic core. Meanwhile, optical Coherence Tomography (OCT) with its high resolution (10-15 µm) has been proposed for detection of thin fibrous cap, macrophages and necrotic core but is not suitable for positive remodelling.

Other emerging methods include intravascular MRI (to detect the necrotic core), angioscopy (to visualise surface appearance of the plaque), thermography (to detect metabolic activity of the plaque) and spectroscopy.

Different types of spectroscopic imaging have been used for the characterization and detection of atherosclerotic plaques. Chemical composition of atherosclerosis has been successfully analysed by Raman spectroscopy and Fourier transform Infrared (FT-IR) spectroscopy in various ex-vivo human atherosclerotic plaques.

Infrared reflection spectroscopy has been shown to be able to differentiate the different plaque components based on their characteristic absorbance/reflectance properties both in-vivo and in-vitro. InfraReDx, Inc. (Burlington, Mass., USA) developed an intracoronary probe using this technique which was later combined with IVUS (LipiScan IVUS system). The SPECTACL (SPECTroscopic Assessment of Coronary Lipid) trial was the first human multicenter study which demonstrated safety and feasibility of detection of lipid core-containing plaques by an intravascular NIRS (Near Infra-Red Spectroscopy) system in living patients.

UV (Ultra-Violet) fluorescence spectroscopy is used as another modality of spectroscopic assessment of atherosclerotic plaques. Some of the components of plaques such as collagen, elastin, some extracellular lipids and ceroids/lipofuscin have been shown to have intrinsic fluorescence when excited by ultraviolet light and visible light in the range of violet and blue (325 to 475 nm). However, UV fluorescence suffers from a number of drawbacks, including photon absorption and substantial tissue autofluorescence, making detection of plaques in this manner problematic.

WO2005/052558 describes methods and apparatus for classifying cancerous tissue using features of Raman spectra and background fluorescent spectra. The spectra may be acquired in the near-infrared wavelengths. Principal component analysis and linear discriminant analysis of reference spectra may be used to obtain a classification function that accepts features of the Raman and background fluorescence spectra for test tissue and yields an indication as to the likelihood that the test tissue is abnormal. The methods and apparatus are applied to screening for skin cancers or other diseases.

SUMMARY OF THE PRESENT INVENTION

In a first broad form the present invention seeks to provide apparatus for use in detecting atherosclerotic plaques, the apparatus including an electronic processing device that:

a) determines a level of fluorescence sensed by a sensing device at a second infrared wavelength in response to exposure of at least part of an artery to radiation at a first infrared wavelength; and, b) determines a fluorescence indicator using the level of fluorescence, the fluorescence indicator being indicative of the presence, absence or degree of an atherosclerotic plaque.

Typically the apparatus includes:

a) a radiation source for generating radiation to thereby expose at least part of the artery to radiation at a first infrared wavelength; and, b) a sensing device for sensing radiation emitted from at least part of the artery at a second infrared wavelength.

Typically the radiation source includes a laser.

Typically the sensing device includes an infrared photodetector.

Typically the apparatus includes optics for focusing radiation.

Typically the apparatus includes a catheter including one or more optical fibres extending between proximal and distal ends, the distal end being for insertion into an artery, and the radiation source and sensing device being coupled to the proximal end.

Typically the apparatus includes a bandpass filter.

Typically the first wavelength is at least one of:
a) 650 nm±50 nm;
b) 700 nm±50 nm;
c) 750 nm±50 nm;
d) 800 nm±50 nm; and,
e) 850 nm±50 nm.

Typically the first wavelength is at least one of:
a) between 650 nm and 900 nm;
b) 685 nm; and
c) 785 nm.

Typically the second wavelength is different to the first wavelength.

Typically the second wavelength is at least one of:
a) 700 nm±50 nm;
b) 750 nm±50 nm;
c) 800 nm±50 nm;
d) 850 nm±50 nm;
e) 900 nm±50 nm;
f) 950 nm±50 nm;
g) 1000 nm±50 nm;
h) 1050 nm±50 nm; and,
i) 1100 nm±50 nm.

Typically the second wavelength is at least one of:
a) between 650 nm and 1144 nm;
b) between 800 nm and 820 nm;
c) 700 nm; and
d) 800 nm.

Typically the electronic processing device:
a) compares the level of fluorescence to a threshold; and
b) determines the fluorescence indicator using the results of the comparison.

Typically the electronic processing device:
a) determines a first level of fluorescence sensed by the sensing device at the second infrared wavelength in response to exposure of a first part of the artery to radiation at the first infrared wavelength;
b) determines a second level of fluorescence sensed by the sensing device at the second infrared wavelength in response to exposure of a second part of the artery to radiation at the first infrared wavelength; and,
c) determines the fluorescence indicator using the first level and the second level.

Typically the electronic processing device:
a) compares the first level to the second level; and,
b) determines the fluorescence indicator using the results of the comparison.

Typically the first part is an at risk part, the at risk part being an area at risk of having an unstable plaque and the second part is a healthy part.

Typically the method includes determining if the first level of radiation is greater than the second level of radiation by a threshold factor of at least 2.

Typically the threshold factor is at least one of:
a) 3 or more;
b) 5 or more;
c) 10 or more; and,
d) 15 or more.

Typically the level of fluorescence is based on an intensity of radiation emitted by the at least one part.

Typically the apparatus is for detecting the vulnerability of atherosclerotic plaque, wherein the fluorescence indicator is indicative of the vulnerability of an atherosclerotic plaque.

Typically the representation includes at least one of:
a) a numerical value indicative of the fluorescence indicator;
b) a symbolic value indicative of the fluorescence indicator;
c) a graphical indicator indicative of the fluorescence indicator; and,
d) an indicator of at least one threshold.

Typically the electronic processing device:
a) determines a detected marker associated with a pathological condition by introducing an agent that detects the marker into the at least part of the artery; and,
b) determines the fluorescence indicator at least partially using the detected marker.

In a second broad form the present invention seeks to provide a method for use in detecting atherosclerotic plaques, the method including, in an electronic processing device:

a) determining a level of fluorescence sensed by a sensing device at a second infrared wavelength in response to exposure of at least part of an artery to radiation at a first infrared wavelength; and, b) determining a fluorescence indicator using the level of fluorescence, the fluorescence indicator being indicative of the presence, absence or degree of atherosclerotic plaques.

In a third broad form the present invention seeks to provide a method for use in detecting vulnerable atherosclerotic plaques, the method including:

a) exposing at least part of an artery to radiation at a first infrared wavelength;

b) determining a level of fluorescence sensed by a sensing device from the at least part of the artery at a second infrared wavelength; and, c) determining a fluorescence indicator using the level of fluorescence, the fluorescence indicator being indicative of the presence, absence or degree of atherosclerotic plaques.

Typically the method includes:

a) introducing an agent that detects a marker into the at least part of the artery, the marker being associated with a pathological condition;

b) determining the detected marker in the at least part of the artery; and, c) determining the fluorescence indicator at least partially using the detected marker.

In a fourth broad form the present invention seeks to provide apparatus for use in analysing fluorescence measurements of atherosclerotic plaques, the apparatus including an electronic processing device that:
- a) determines a level of fluorescence sensed by a sensing device at a second infrared wavelength, the radiation being sensed in response to exposure of an atherosclerotic plaque to radiation at a first infrared wavelength; and,
- b) determines a fluorescence indicator using the level of fluorescence, the fluorescence indicator being indicative of a degree of fluorescence of the atherosclerotic plaque.

In a fifth broad form the present invention seeks to provide a method for use in analysing fluorescence measurements of atherosclerotic plaques, the method including, in an electronic processing device:
- a) determining a level of fluorescence sensed by a sensing device at a second infrared wavelength, the radiation being sensed in response to exposure of an atherosclerotic plaque to radiation at a first infrared wavelength; and,
- b) determining a fluorescence indicator using the level of fluorescence, the fluorescence indicator being indicative of a degree of fluorescence of the atherosclerotic plaque.

In a sixth broad form the present invention seeks to provide apparatus for use in detecting the vulnerability of atherosclerotic plaques, the apparatus including:
- a) a radiation source for generating radiation to thereby expose at least part of the artery to radiation at a first infrared wavelength;
- b) a sensing device for sensing radiation emitted from at least part of the artery at a second infrared wavelength;
- c) an electronic processing device coupled to the sensing device that:
  - i) determines a level of fluorescence sensed by the sensing device; and,
  - ii) determines a fluorescence indicator using the level of fluorescence, the fluorescence indicator being indicative the vulnerability of an atherosclerotic plaque.

Typically the apparatus includes a catheter including one or more optical fibres extending between proximal and distal ends, the distal end being for insertion into an artery, and the radiation source and sensing device being coupled to the proximal end.

BRIEF DESCRIPTION OF THE DRAWINGS

An example of the present invention will now be described with reference to the accompanying drawings, in which:—

DETAILED DESCRIPTION OF THE PREFERRED EMBODIMENTS

Figure 1A:
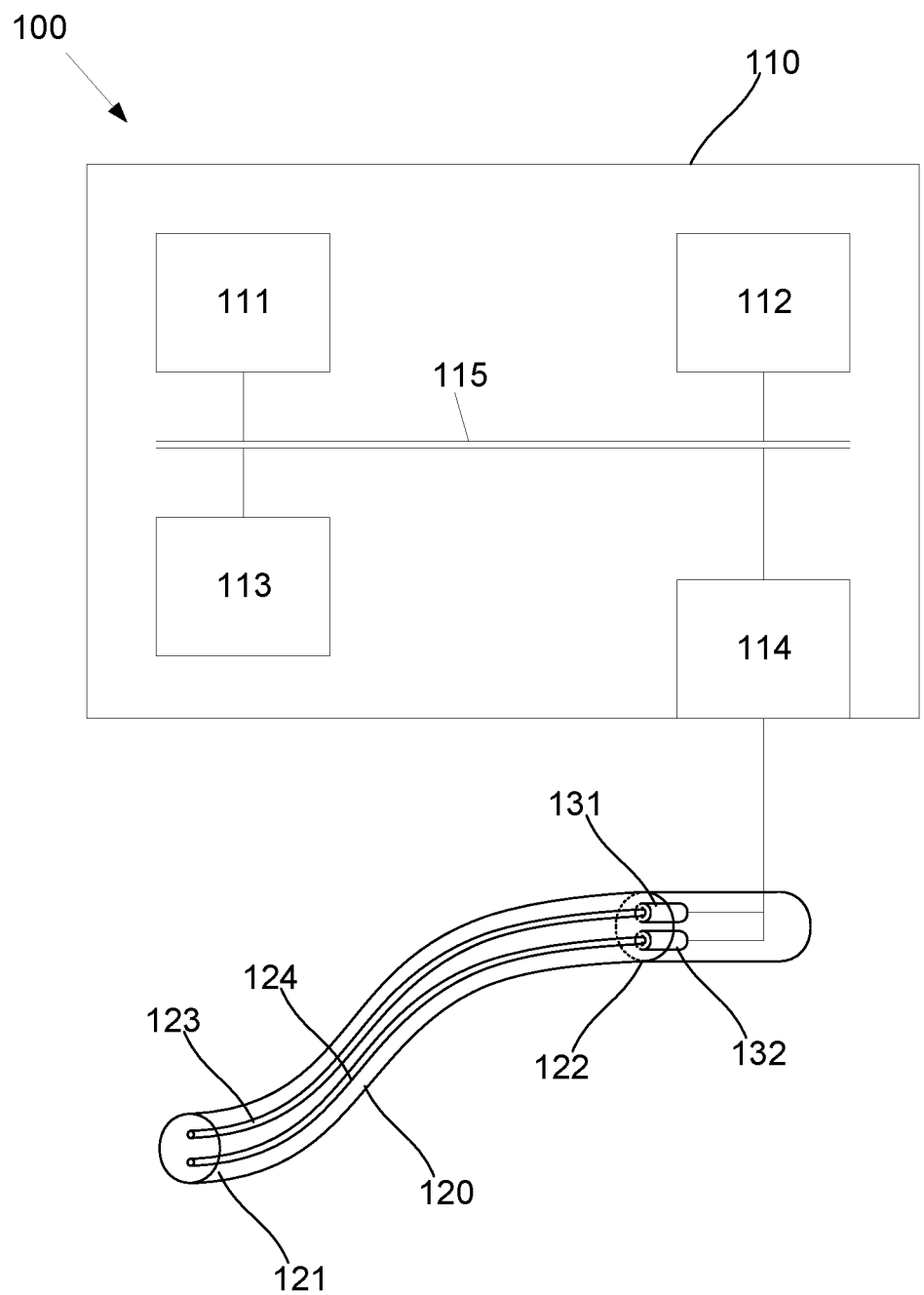
FIG. 1A is a schematic diagram of a first example of an apparatus for use in detecting atherosclerotic plaques.
Figure 1B:
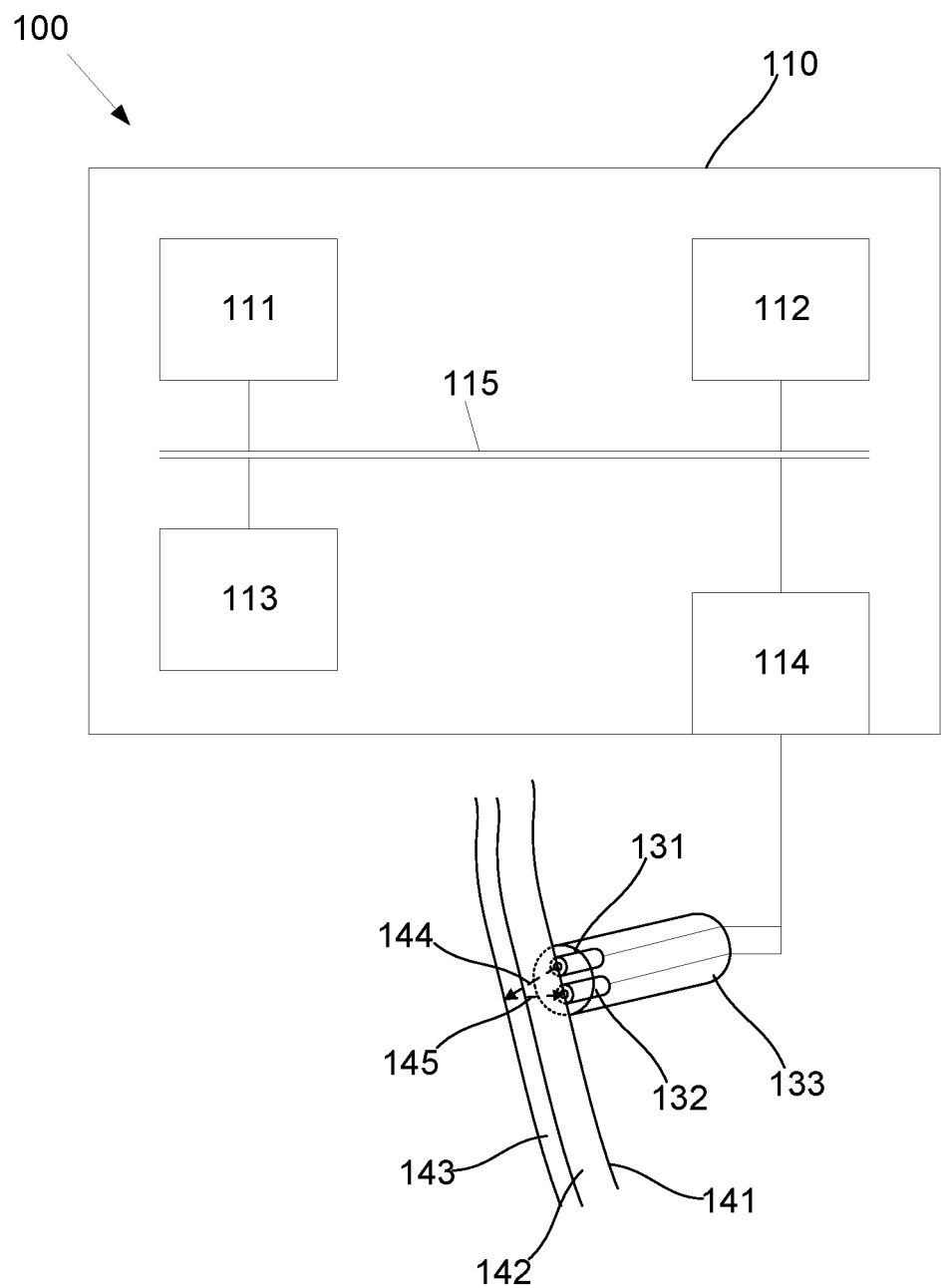
FIG. 1B is a schematic diagram of a second example of an apparatus for use in detecting atherosclerotic plaques.

An example of an apparatus for use in detecting atherosclerotic plaques will now be described with reference to FIGS. 1A and 1B.

In this example, the apparatus 100 includes a processing system 110 including an electronic processing device, such as a processor 111, that determines a level of fluorescence sensed by a sensing device at a second infrared wavelength in response to exposure of at least part of an artery to radiation at a first infrared wavelength and determines a fluorescence indicator using the level of fluorescence, the fluorescence indicator being indicative of the presence, absence or degree of an atherosclerotic plaque.

Thus, the above described apparatus is capable of analysing a level of infrared fluorescence determined by a sensing device, and using this to detect a presence, absence or degree of an atherosclerotic plaque. In one particular example, this can be used to provide an indicator that can be used by a practitioner to ascertain the degree of vulnerability of a detected atherosclerotic plaque, hence allowing a medical practitioner to identify a suitable treatment regime.

Sensing of fluorescence is typically carried out in response to exposure of a suspected atherosclerotic plaque to infrared radiation of a first wavelength, with detection of fluorescence being performed at a second different infrared wavelength. This is performed to allow radiation used to expose the tissue to be distinguished from fluorescence, and in particular to prevent exposing radiation causing a spurious result. However, exposing radiation and fluorescence can be distinguished in other manners, for example using a time resolved technique. In particular, there is a small time delay between exposure of tissue and subsequent generation of fluorescence, typically in the order of a few nano-seconds. Accordingly, the sensing device can be adapted to only detect radiation after the radiation source has ceased emitting radiation, for example using a gated sensing device, thereby ensuring that detected radiation includes only radiation resulting from fluorescence.

The manner in which exposure and sensing is performed will depend on the circumstances in which the analysis is performed, and will for example depend on whether this is performed in-vivo, ex-vivo, or in-vitro.

In one example, for use in-vivo, for example on the coronary artery, the apparatus 100 can farther include a catheter 120 including two optical fibres 123, 124 extending between distal and proximal ends 121, 122. A radiation source 131, such as a laser or laser diode, is coupled to the proximal end 122, and in particular is optically coupled to the optical fibre 123. A sensing device 132, such as a photodetector, photomultiplier, infrared camera, or the like, is coupled to the proximal end 122, and in particular is optically coupled to the optical fibre 124. The catheter 120 may also include optics provided at the distal end 121, allowing radiation to be emitted from, or received by the optical fibres 123, 124, as required.

It will be appreciated that the catheter 120 may also include other components, such as a manipulator, to control insertion of the catheter, and one or more imaging systems, such as an endoscope, OCT sensor, or the like, to ascertain catheter placement, or determine a location indicator and this will be described in further detail below.

Optionally, the catheter 120 may further include any one or more of a guide wire for guiding insertion of the catheter into a subject, a proximal and distal marker for indicating insertion depth of the catheter, a coating to aid insertion and manipulation such as an hydrophilic coating, a lumen for optionally injecting contrast agents, performing interventions, or the like, a tapered catheter tip for aiding insertion. In any event, it will be appreciated that further catheter components are known in the art, these will not be described in further detail.

In this example, each of the detector 131 and sensing device 132 are coupled to respective optical fibres 123, 124, allowing radiation to be transmitted in each direction along the catheter 120, via respective transmission paths. However, this is not essential, and alternatively the radiation source 131 and sensing device 132 may transmit and receive radiation via a single optical fibre as will be appreciated by a person skilled in the art.

In use, the distal end 121 is adapted to be inserted into the artery of a subject. The radiation source 131 generates radiation at the first infrared wavelength, allowing this to the transmitted via the optical fibre 123, to thereby expose at least part of the artery to the radiation. Fluorescence radiation emitted by the artery is then transmitted via the optical fibre 124 to the sensing device 132, allowing fluorescence of at least part of the artery at a second infrared wavelength to be sensed.

In one particular example, the catheter 120 may include a catheter tip provided at the distal end 121, a catheter body, and a controller system. In particular, the catheter tip is configured to expose at least part of an artery to radiation at one or more first infrared wavelengths at an optimal depth of focus, and to sense a level of fluorescence at one or more second infrared wavelengths with sufficient sensitivity to determine a fluorescence indicator using the level of fluorescence, the fluorescence indicator being indicative of the presence, absence or degree of an atherosclerotic plaque, for example, indicative of the vulnerability of the plaque, such as being at high risk of rupture or rupture prone.

The catheter body may provide for controlled rotation and longitudinal movement under control of the controller system as described below, and may provide optical and/or electrical connectivity between rotational and stationary elements of the apparatus. In addition, the controller system may include an electronic processing device substantially as described above, a power supply, an optical source and optical detection, and an optional motor drive for rotation and potentially pullback, in order to provide the controlled rotation and longitudinal movement of the catheter body.

In this regard, catheters including suitable a catheter tip, a catheter body, and controller system functionalities such as described above exist in fields such as coronary imaging. However, this particular catheter arrangement is not essential, and any suitable apparatus for determining a level of fluorescence as described may be used.

It will also be appreciated by persons skilled in the art that other techniques could be used for exposing part of an artery to radiation, and in this respect the term radiation would be understood to include irradiating part of the artery or any other suitable technique of exposing to radiation. For example, as shown in FIG. 1B, the radiation source 131 and sensing device 132 can be mounted in a housing 133, which in use is positioned against a subject's skin surface 141. In this instance, radiation emitted from the radiation source 131 passes through the skin and underlying tissue 142 and into an artery 143, as shown by the arrow 144, allowing fluorescence radiation to be returned to the sensing device 132, as shown by the arrow 145. In this arrangement, suitable optics may also be provided either as part of the housing 133, or the radiation source 131 and sensing device 132, allowing focusing of radiation as required.

Accordingly, it will be appreciated that this arrangement allows exposure of part of an artery to be performed by having radiation transmitted through the subject's tissue. This allows detection of atherosclerotic plaques to be performed for arteries near a subject's skin, such as the carotid artery, without requiring invasion of the subject.

In either of the above described cases, the processing system 110 typically operates to receive signals from the sensing device 132 indicative of the level of fluorescence detected in the artery, and uses this to determine the fluorescence indicator, as will be described in more detail below. The processing system 110 may also optionally be used to control the radiation source 131, to thereby selectively expose the artery to radiation.

In one example, the processing system includes a processor 111, a memory 112, an input/output (I/O) device 113, such as a keyboard and display, and an external interface 114 interconnected via a bus 115. The external interface 114 can be used for coupling the processing system 110 to the radiation source 131 or the sensing device 132, as well as to other peripheral devices, such as communications networks, databases, other storage devices, or the like. Although a single external interface is shown, this is for the purpose of example only, and in practice multiple interfaces using various methods (e.g. Ethernet, serial, USB, wireless, mobile networks or the like) may be provided. It will also be appreciated that additional hardware components, may be incorporated into the computer system 110, depending on the particular implementation.

In use, the processor 111 operates in accordance with input commands and/or instructions in the form of applications software stored in the memory 112, to allow signals from the sensing device 132 to be interpreted and optionally used, for example to detect or quantify the vulnerability of atherosclerotic plaques, as will be described in more detail below. Accordingly, for the purposes of the following description, it will be appreciated that actions performed by the processing system 110 are typically performed by the processor 111 under control of instructions stored in the memory 112, and this will not therefore be described in further detail below.

It will be further appreciated that the computer system 110 may be formed from any suitably programmed processing system, such as a suitably programmed PC, Internet terminal, lap-top, hand-held PC, tablet PC, slate PC, iPad™, mobile phone, smart phone, PIM (Personal Data Assistant), or other processing device. Accordingly, the processor 111 can be any form of electronic processing device such as a microprocessor, microchip processor, logic gate configuration, firmware optionally associated with implementing logic such as an FPGA (Field Programmable Gate Array), or any other electronic device, system or arrangement capable of interacting with the sensing device 132 and optionally the radiation source 131.

It will also be appreciated that whilst a single physical processing system is shown, multiple processing systems could be used, with for example some preliminary processing being performed in custom configured hardware, such as an FPGA, and with the generation and display of a fluorescence indicator being performed using a general purpose computer system.

Operation of the apparatus 100 for use in detecting atherosclerotic plaques will now be described with reference to FIG. 2.

In this example, at step 200, part of an artery is exposed to radiation at a first infrared wavelength, the radiation being generated by the radiation source 131, and transmitted into the artery via the catheter 120. At step 210, the sensing device 132 operates to sense fluorescence radiation emitted from the part of the artery at a second infrared wavelength which is different to the first infrared wavelength, for example, the second infrared wavelength may be longer than the first infrared wavelength.

At step 220, the processing system 110 uses signals acquired from the sensing device 132 to determine a level of fluorescence, which is then used to determine a fluorescence indicator at step 230. The fluorescence indicator can be determined using any suitable technique, and may therefore be based on an absolute, relative or normalised intensity of fluorescence. Alternatively, the fluorescence indicator can be determined at least in part based on a comparison of the detected fluorescence to a threshold, such as one or more reference values, as will be described in more detail below.

At step 240, a representation of the fluorescence indicator may optionally be displayed allowing this to be used by a medical practitioner, for example in diagnosing the presence, absence, degree or vulnerability of atherosclerotic plaque.

The nature of the fluorescence indicator and, in particular the manner in which it is displayed to an operator, will vary depending upon the preferred implementation. In one example, the fluorescence indicator is in the form of a numerical value, indicative of the absolute level of fluorescence. Alternatively however, a symbolic value, such as including letters or other symbols, or a graphical indicator can be displayed which is representative of the numerical value. Additionally, an indication of a threshold and optionally the result of a comparison thereto can be displayed allowing this to be used by a medical practitioner in order to assist in diagnosing the presence, absence or degree of vulnerability of an atherosclerotic plaque.

It will be appreciated that whilst the above described method and apparatus arrangements are described for use in-vivo, alternatively the apparatus and method could be performed in-vitro, on samples excised from a subject. In this example, the catheter is not required and the processing system 110, radiation source 131, and sensing device 132 can form part of an infrared imaging system, which can be used to acquire fluorescence information from section samples, as will be described in more detail below.

In any event, it has been discovered that if atherosclerotic plaques are exposed to infrared radiation, they can undergo auto-fluorescence, depending on the status, and in particular the stability or vulnerability of the plaque. In this regard, if plaques are stable, the level of auto-fluorescence is minimal. However, if plaques are unstable, commonly referred to as "vulnerable", then the degree of auto-fluorescence is significantly increased. As a result, by determining a fluorescence indicator, this can be indicative of the presence, absence or degree of an atherosclerotic plaque, for example, indicative of the vulnerability of the plaque, such as being at high risk of rupture or rupture prone.

Accordingly, the above described method and apparatus can be used to allow a fluorescence indicator to be derived based on the fluorescence of at least part of an artery, in response to exposure by infrared radiation. The part of the artery is typically a part including a lesion, and can be analysed in situ, or can be excised from the subject and analysed remotely. The level of fluorescence can be used to derive a fluorescence indicator, which can in turn be indicative of the presence, absence or degree of stability of an atherosclerotic plaque.

Accordingly, this provides a straightforward method to allow medical practitioners to identify, and subsequently classify atherosclerotic plaques, in turn allowing the medical practitioner to assess what if any treatment may be required. Furthermore, this process relies on autofluorescence of the plaque, avoiding the need for the introduction of external markers, such as fluorochromes targeting some specific molecules (such as proteases) in the plaques.

A number of further features will now be described.

In one example, the first wavelength is typically between 650 nm and 900 nm. In one particular example, the first wavelength is either 685 nm or 785 nm, although it will be appreciated that other wavelengths may be used. Similarly, the second wavelength is typically in the region of 650 nm to 1144 nm particularly is typically either 700 nm or 800 nm, or in the range 800 nm to 820 nm. The wavelengths are selected to maximise the fluorescent responsive of the plaques, as will be described in more detail below.

In some embodiments, the first wavelength is in a range selected from: 650 nm-850 nm, 700 nm-850 nm, 750 nm-850 nm, 800 nm-850 nm, 650 nm-800 nm, 700 nm-800 nm, 750 nm-800 nm, 650 nm-700 nm, 650 nm-750 nm, 650 nm-800 nm, or 700 nm-750 nm.

In some embodiments, the second wavelength is in a range selected from: 700 nm-1150 nm, 750 nm-1150 nm, 800 nm-1150 nm, 850 nm-1150 nm, 900 nm-1150 nm, 950 nm 1150 nm, 1000 nm-1150 nm, 1050 nm-1150 nm, 1100 nm-1150 nm, 700 nm-1100 nm, 750 nm 1100 nm, 800 nm-1100 nm, 850 nm-1100 nm, 900 nm-1100 nm, 950 nm-1100 nm, 1000 nm-1100 nm, 1050 nm-1100 nm, 700 nm-1050 nm, 750 nm-1050 nm, 800 nm-1050 nm, 850 nm-1050 nm, 900 nm-1050 nm, 950 nm-1050 nm, 1000 nm-1050 nm, 700 nm-1000 nm, 750 nm-1000 nm, 800 nm-1000 nm, 850 nm-1000 nm, 900 nm-1000 nm, 950 nm-1000 nm, 700 nm-950 nm, 750 nm 950 nm, 800 nm-950 nm, 850 nm-950 nm, 900 nm-950 nm, 700 nm-900 nm, 750 nm-900 nm, 800 nm-900 nm, 850 nm-900 nm, 700 nm-850 nm, 750 nm-850 nm, 800 nm-850 nm, 700 nm-800 nm, 750 nm-800 nm or 700 nm-750 nm.

It will be understood that the term "between" when used in reference to a range of numerical values encompasses the numerical values at each endpoint of the range. For example, a wavelength of between 650 nm and 900 nm is inclusive of a wavelength of 650 nm and a wavelength of 900 nm.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Each embodiment described herein is to be applied mutatis mutandis to each and every embodiment unless specifically stated otherwise.

As mentioned above, the catheter may include optical elements in order to allow suitable focusing of radiation within the artery and detection therefrom. Additionally, the apparatus may include bandpass filters for filtering radiation emitted from the radiation source or to be received by the sensing device to thereby limit unwanted background signals.

In order to determine the fluorescence indicator, the processing system 110 may perform a partial assessment of the level of fluorescence, for example by comparing this to a threshold and determining whether the level of fluorescence exceeds or falls below the threshold. This can be used to indicate a state or, in particular, a degree of vulnerability of an atherosclerotic plaque.

Additionally, and as will be described in more detail below, the processing system 110 may operate to compare the level of fluorescence detected at a healthy site to the level of fluorescence detected at a site where there is a suspected atherosclerotic plaque, which can in turn be used confirm whether an atherosclerotic plaque is present, and optionally the degree of vulnerability.

A second example of the process for use in detecting atherosclerotic plaques will now be described with reference to FIG. 3. During this process, it is assumed that the processing system 110 is executing applications software for controlling the radiation source 131 and for analysing signals from the sensing device 132.

In this example, at step 300, the catheter is introduced into the artery of a subject, with the distil end 121 of the catheter 120 being positioned adjacent a part of the artery to be measured. Typically, this is a part of the artery which is thought to be at risk of having a vulnerable plaque.

At step 305, a first part of the artery is exposed to radiation at the first wavelength. Typically this is achieved by having an operator provide an input command to the processing system 110, confirming that the catheter is positioned as required, allowing the processing system 110 to activate the radiation source 131. At step 310, the processing system 110 acquires signals from the sensing device 132 that are indicative of the level, and in particular the intensity, of fluorescence in the first part of the artery.

At step 315, the processing system 110 determines if fluorescence in a second part of the artery is to be determined. This can be achieved depending on a selected measurement protocol, or in accordance with an input command from an operator. This is typically performed to allow a comparison to be performed between readings at different locations within the artery, for example to assist in establishing if a fluorescence level is indicative of a vulnerable plaque or to take into account background levels of fluorescence in healthy tissue.

In this regard, the fluorescence in the second part of the artery may be determined at any suitable part of the artery, or alternatively other blood vessels, or a phantom vessel that includes fluorescence properties analogous to healthy tissue, stable and/or unstable plaques. In one example, a location of the second part of the artery, or other vessel, which includes substantially healthy tissue or a stable plaque, may be determined based upon a location indicator, such as an image. In this respect, the method includes determining a location indicator, and determining fluorescence in the second part of the artery using at least partially the location indicator. In this respect, the image may be acquired according to any suitable internal or external imaging modality, such as angiography, x-ray, video imaging, OCT, computed tomography (CT), magnetic resonance imaging (MRI), near infrared spectroscopy (NIR), Raman spectroscopy, UV fluorescence, or the like.

In a further example, the second part of the artery may correspond to a location in the artery, or other vessel, which typically includes a low or lower probability of exhibiting vulnerable plaques, such as, based on a sample population, a scientific inference, or the like. For example, in a population with heart disease, typically few unstable plaques develop in at least some of the arteries in the arm.

Additionally, the second level of fluorescence may be determined based on a plurality of measurements that are indicative of the level of fluorescence, where the measurements are acquired as discussed in any one of the above examples. In this respect, the plurality of measurements may correspond to a plurality of parts of the artery or another vessel, and hence the second level of fluorescence may be based on an average, median, mode, or other suitable indicator indicative of the plurality of measurements. In one example, the plurality of measurements are determined at a plurality of parts of the femoral artery, however this is not essential, and the plurality of measurements may be determined in different parts of any suitable vessel/s, or alternatively at different times in the same part of the artery or other vessel.

Alternatively, the intensity of the fluorescence may be compared to a threshold, for example the threshold may be indicative of the intensity of the fluorescence of healthy tissue or a stable plaque, and this is discussed in more detail below.

It will be appreciated that these steps, for example determining a location indicator, determining an average of a plurality of measurements, and the like, may not be limited to determining the second level of fluorescence and in this respect may also be applied in any of the above examples, such as determining the first level of fluorescence. For example, a location of the first part of the artery to be tested may be determined using a location indicator.

At step 320, if no other part is to be examined, the intensity of fluorescence can be compared to a threshold. The threshold may be established based on measurements from reference samples of vulnerable and stable atherosclerotic plaques, identified by histological examination, previous in vivo measurements from a sample population, previous measurements on the first part of the artery, previous measurements from other blood vessels of a same or similar subject, or any other suitable technique.

This allows a threshold to be established which is indicative of whether an atherosclerotic plaque is vulnerable. It will be appreciated that multiple thresholds could also be established to allow a degree of vulnerability to be established. Alternatively, the intensity of fluorescence can be analysed using any other suitable approach.

At step 325, a representation of a fluorescence indicator is displayed, for example using the I/O device 113. The fluorescence indicator can be a numerical or graphical representation of the intensity of fluorescence and/or the result of the comparison to a threshold. An indication of the threshold may also be displayed, allowing the medical practitioner viewing the results to make an easy assessment of whether a vulnerable atherosclerotic plaque exists. A visual indication of an image of the fluorescence may also be displayed, assuming the sensing device is capable of capturing an image.

In the event that a second part of the artery is to be examined, the processing system 110 can generate an instruction to the medical practitioner operating the catheter causing them to reposition the catheter at step 330. The practitioner can confirm once this has been completed, by providing an appropriate input command, allowing the processing system 110 to activate the radiation source 131 and expose the second part of the artery to radiation at step 335. At step 340, the processing system 110 acquires signals from the sensing device 132 that are indicative of a second level, and in particular intensity, of fluorescence in the second part of the artery.

At step 345, the processing system determines a difference in the first and second levels of fluorescence, for example by subtracting one value from the other, by determining a ratio between the first and second levels of fluorescence, or the like. This allows the impact of fluorescence in a healthy part of the artery, representing a background fluorescence, to be taken into account. In this regard, the term healthy part is taken to include a part of the artery without any plaque and/or parts of the artery including stable and/or non-vulnerable plaques. At step 350 the difference in intensity can be compared to a threshold, which again may be established based on measurements from reference samples, as will be described in more detail below.

At step 325, the fluorescence indicator can be displayed substantially as described above, allowing the fluorescence indicator to be interpreted by the medical practitioner, and in particular to allow the medical practitioner to assess the degree of vulnerability of any atherosclerotic plaque, and hence assess whether any intervention is required.

It will be appreciated that a number of variations of the above described process may be implemented. For example, the or each part of the artery can be exposed to radiation at a number of different first wavelengths, with the fluorescence being measured at a corresponding number of different second wavelengths. This can be used to help further classify the nature of any atherosclerotic plaque. Furthermore, multiple different thresholds can be used to allow the vulnerability of the plaques to be accurately identified.

The method may further include, for example, detecting a marker associated with a pathological condition and using the detected marker, for instance as a guide, to determine the fluorescence indicator in the at least part of the artery. Suitably, the marker is detected by introducing an agent that detects the marker, into the at least part of the artery.

In this respect, the detected marker may provide a location indictor for, or guide to the position of, healthy tissue, one or more stable plaques, and/or one or more unstable plaques. Additionally or alternatively, the detected marker may be used with the level of fluorescence to determine the fluorescence indicator, such as by weighting the level of fluorescence in accordance with a numerical value indicative of the detected marker.

In one example, the pathological condition is associated with presence or risk of an unstable plaque, and in this regard the marker may include any one or more of a cell, cell debris, tissue damage, cellular components, chemicals, or the like. In this respect, the pathological condition may include activated platelets, the marker may include a glycoprotein IIb/IIIc receptor and the agent may include an anti-LIES (ligand induced binding site) antibody or microparticles of iron oxide (MIPO), for example for targeting LIRSs of the glycoprotein IIb/IIIa receptor. In a further example, the pathological condition may include inflamed endothelial tissue, and in this respect the agent may include an anti-interleukin-1 antibody and the marker may include interleukin-1. However, this is not essential, and optionally the marker may be associated with stable plaques, or healthy tissue, or alternatively no agent may be used.

In addition, determining the detected marker may be achieved in any suitable manner, for example an image of the detected marker may be acquired using an imaging modality corresponding to the properties of the detected marker. In this respect the imaging modality may include fluorescence, x-ray, computed tomography (CT), gamma-scintigraphy, positron emission tomography (PET), single photon emission computed tomography (SPECT), MRI, and combined imaging techniques.

Experimental evidence of the effectiveness of the above described auto-fluorescence of vulnerable plaques will now be described.

For the purpose of a first experimental example, animal data is derived using a "tandem stenosis model" of atherosclerosis in mice, which closely resembles the atherosclerosis process in humans.

A surgical ligation procedure (serial ligation of segments of the carotid arteries) was performed to create a tandem stenosis to the carotid artery of ApoE$^{-/-}$ mice fed with high fat diet. After 7 and 11 weeks postoperatively, disruption of fibrous caps, intraplaque haemorrhage, intraluminal thrombosis, neovascularisation and other characteristics of plaque instability/rupture in humans were seen in these mice.

Figure 4A:
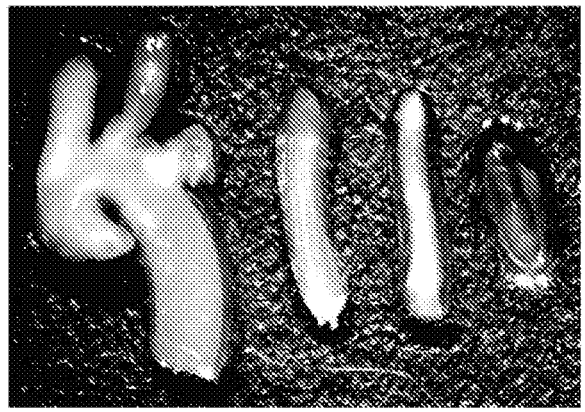
FIG. 4A is an image of samples from mice models defined by histological examination.

The fresh carotid artery specimens from these mice, shown in FIG. 4A, were examined for autofluorescence under an Odyssey Infrared Imaging System which has 2 excitation channels 685 nm (detection on 700 nm) and 785 nm (detection 800 nm). Vulnerable plaques were identified by histological examination.

Figure 4B:
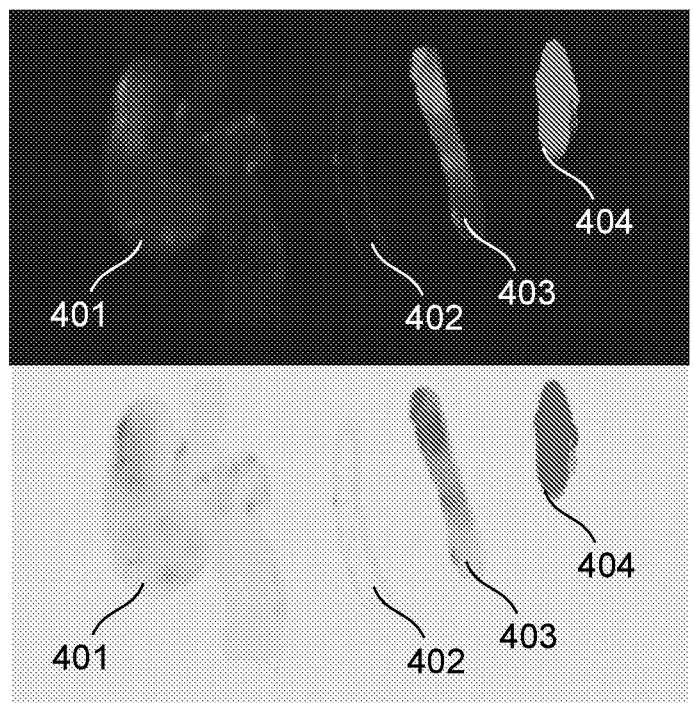
FIG. 4B shows positive and negative images of NIR (Near Infra-Red) Fluorescence of the samples of FIG. 4A.

The results of fluorescence imaging are shown in FIG. 4B, which shows minimal autofluorescence in stable atherosclerotic plaque in aortic arch and carotid arteries 401, no autofluorescence in healthy carotid artery 402, significant autofluorescence in an unstable carotid plaque with intraplaque haemorrhage 403 and significant autofluorescence in a vulnerable carotid plaque with positive remodelling 404. Thus, the vulnerable atherosclerotic plaques 403, 404 show significant autofluorescence in both channels, in contrast to the healthy vessels and stable plaques 401, 402, which showed no intrinsic fluorescence.

For the purpose of a second experimental example, human data is derived from patients undergoing carotid endarterectomy at the Alfred Hospital (Melbourne, Australia). The project was approved by the Alfred Ethics Committee. Carotid endarterectomy specimens were collected immediately after being excised from the patients.

Figure 5A:
FIG. 5A is an image of an example of a freshly excised carotid endarterectomy specimen.
Figure 5B:
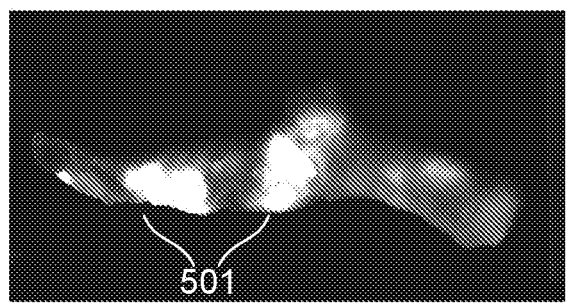
FIG. 5B shows positive and negative images of NIR Fluorescence of the specimen of FIG. 5A.
Figure 5B:
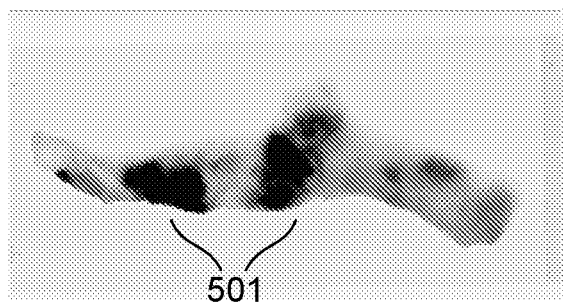

Freshly excised carotid endarterectomy specimens, an example of which is shown in FIG. 5A, were placed on the glass slides and examined for autofluorescence under an Odyssey Infrared Imaging System as described above. As shown in FIG. 5B, the areas of the vulnerable atherosclerotic plaques 501 showed significant autofluorescence in both channels in contrast to the areas of normal intima and stable plaques, which showed no intrinsic fluorescence.

Figure 5C:
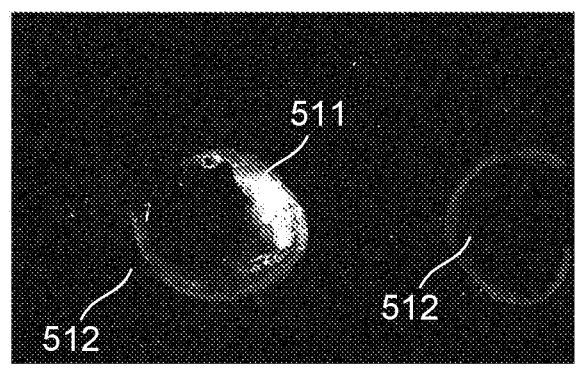
FIG. 5C shows positive and negative NIR Fluorescence images of a cryosectioned excised carotid endarterectomy specimen.
Figure 5C:
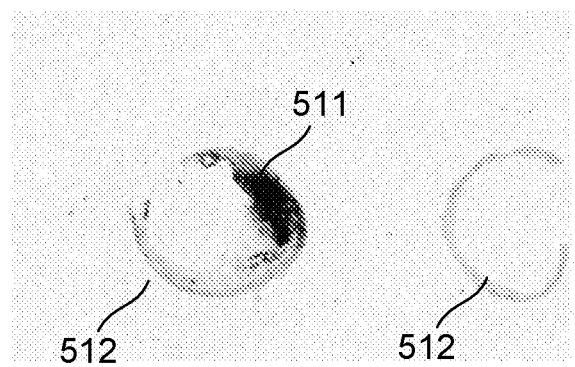

The fresh carotid endarterectomy specimens were then snap-frozen and kept at −80° C. Parts of the snap-frozen specimens were then embedded in an optimal cutting temperature compound for cry sectioning. 5 µm tissue sections were performed and examined for autofluorescence under Odyssey Infrared Imaging System. As shown in FIG. 5C, only areas of vulnerable plaques 511 but not stable and normal areas 512 were found to have significant autofluorescence in both channels of excitation and emission as above.

Figure 5D:
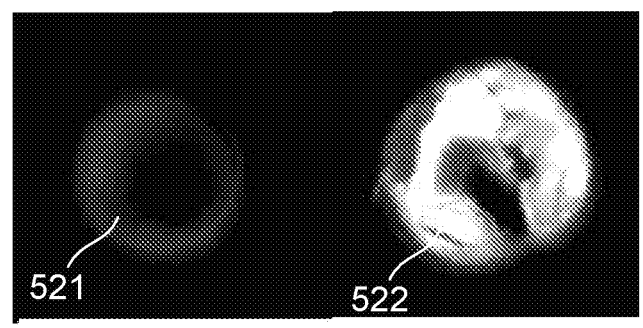
FIG. 5D shows positive and negative NIR Fluorescence images of a stable and vulnerable paraffin-embedded excised carotid endarterectomy specimen.
Figure 5D:
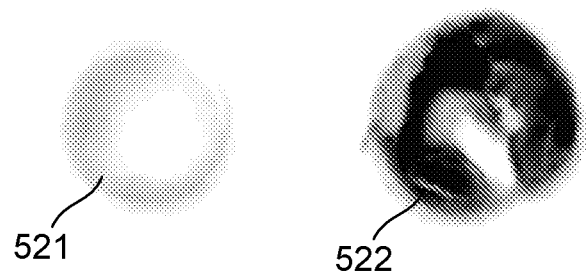

Parts of the snap-frozen specimens were treated with 10% formalin and then embedded in paraffin. 5 µm tissue sections were examined for autofluorescence as shown in FIG. 5D, with autofluorescence of stable plaque 521 compared to vulnerable plaque 522.

Figure 6A:
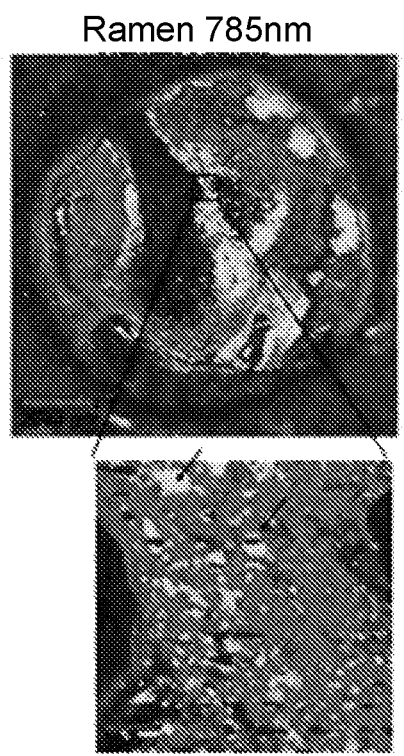
FIG. 6A shows example images of autofluorescence of areas of vulnerable plaques on excitation with 785 nm radiation (Raman spectrometer)
Figure 6B:
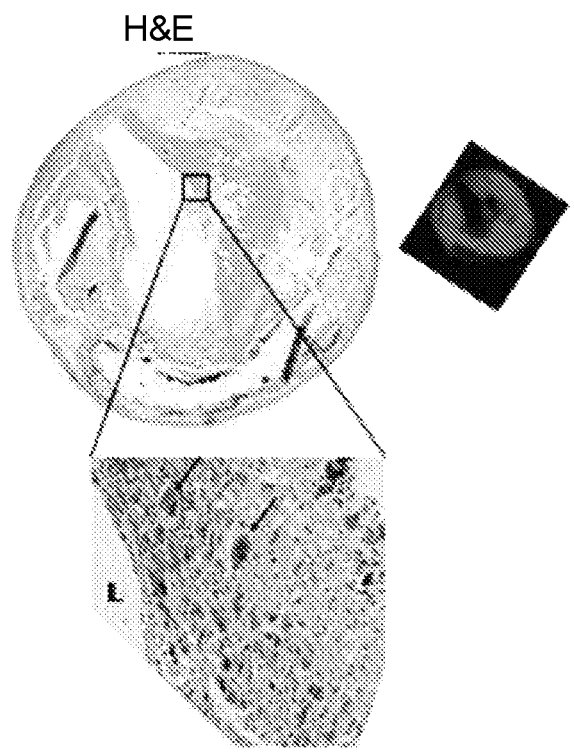
FIG. 6B shows example images of vulnerable plaques with H&E staining showing infiltration of inflammatory cells and some intraplaque haemorrhage (right)

For the purpose of a third experimental example, shown in FIGS. 6A and 6B, analysis of atherosclerotic plaques using an AFM Raman Spectrometer. This experiment used an NT-MDT Integra AFM Raman System with two Raman laser sources (532 nm and 785 nm excitation) was then used to confirm the autofluorescence of these vulnerable plaques.

Paraffin embedded sections were excited with 785 nm laser source and the emission was studied throughout the whole detection range (from 800 nm to 1144 nm). The strongest signal of emission was detected between 800-820 nm on AFM Raman system.

In a fourth experimental example, an Odyssey Infrared Imaging System was used to quantify the fluorescence detected from healthy tissue and unstable plaques. In this example, samples used were fresh macroscopic carotid endarterectomy tissues, which were scanned immediately after being taken out from the patient. The imager was used to scan the tissues with 21 µm resolution and at an intensity setting of "4" using both 700 nm and 800 nm excitation and detection channels. The images taken were then normalised with gamma≅1.

An example of the measured intensities for healthy tissue and unstable plaques are shown in Table 1 below.

Accordingly, the above study of 20 human plaques demonstrates a 9.88+/−7.5 (mean±SD) fold difference in intensity between healthy tissue and unstable plaques.

It will be appreciated from this, that by comparing the intensity of fluorescence measured for a plaque of unknown status (unknown plaque) to a healthy reference, this allows the stability of the unknown plaque to be assessed. In particular, if the measured level of fluorescence for the unknown plaque is greater than the level of fluorescence from an artery with no plaque or a stable plaque, by a threshold factor generally of at least 2, and typically of at least 3, at least 5, at least 10 or at least 15, then this can be used to determine if the unknown plaque is unstable, and if so the degree of stability.

It will be appreciated that the value of the factor of increase in fluorescence intensity for a healthy sample, or an unstable plaque, can be further refined based on additional sample data, and that by collecting data from reference samples having different degrees of stability, this will allow thresholds for different degrees of stability to be identified.

Whilst not wishing to be bound by any particular theory or mode of action, it has been discovered following experimentation that autofluorescence in unstable plaques may be at least partially caused by a molecular species including haeme-degradation products, for example, haeme, methaeme, and protopozphyrin IX. In view of this, the experimental evidence may suggest an at least partial correlation between haeme-degradation products and autofluorescence of unstable plaques, and this will now be described.

Figure 7A:
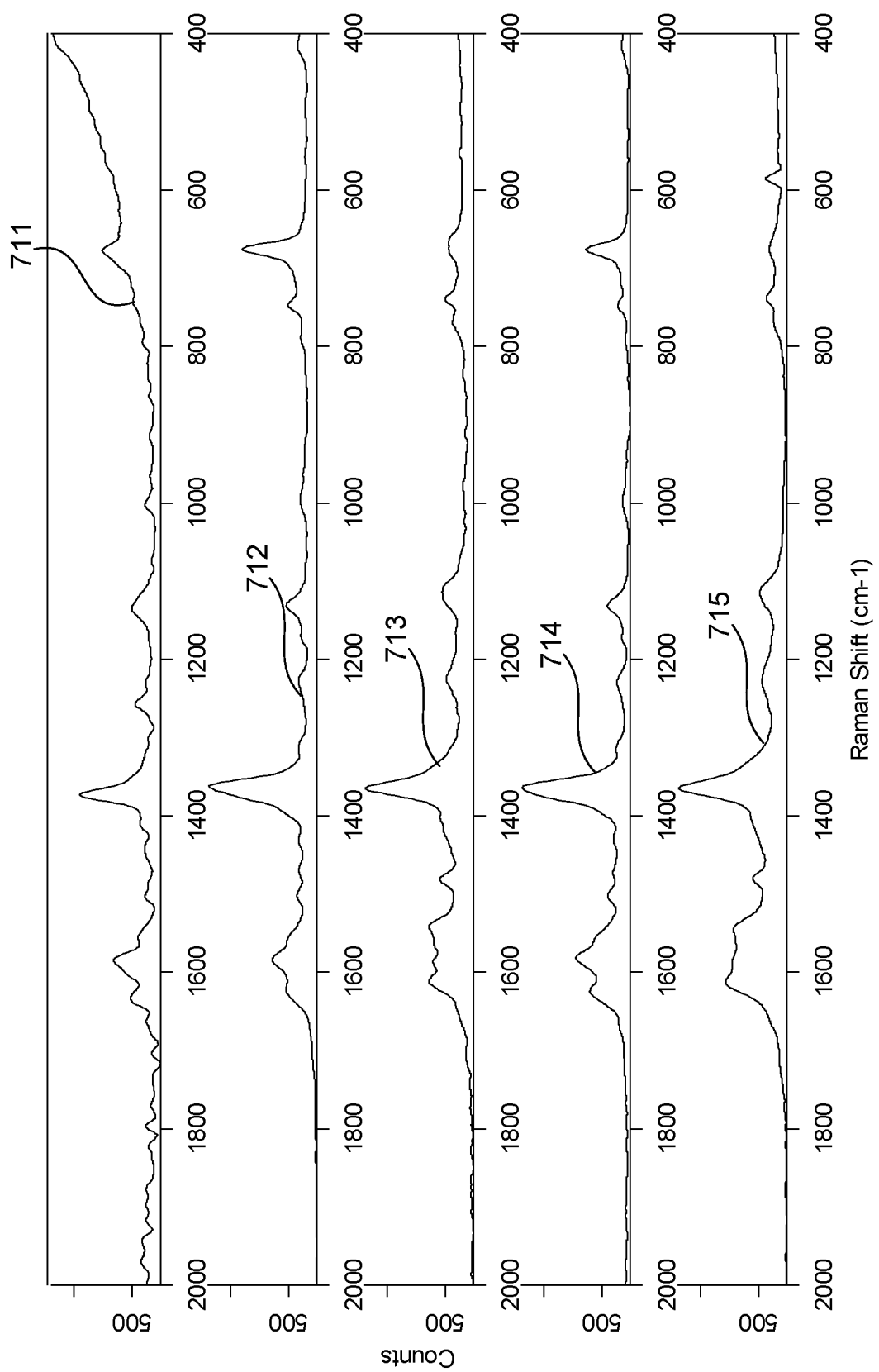
FIG. 7A is a trace of an example of Raman signals from an area of fluorescence in a vulnerable plaque section in comparison with Raman signals from purified haeme, methaeme and protoporphrin IX compounds.

Renishaw Invia confocal micro-Raman system using Raman laser source of Innova Ar/Kr ion laser 514/413 nm was used to assess Raman signals from the areas of autofluorescence in the vulnerable plaque sections. The Raman signals reveal that the source of autofluorescence is haeme-degradation products, which are abundant in the areas of intraplaque haemorrhage (microscopic or macroscopic). Intraplaque haemorrhages are well established as the triggers for plaque vulnerability (Jean-Baptise Michel et al. (2011) *Eur Heart J.* 32(16): 1977-85). FIG. 7A is an example of Raman signals from the area of fluorescence 711 in the vulnerable plaque section in comparison with Raman

TABLE 1

Figure 7B:
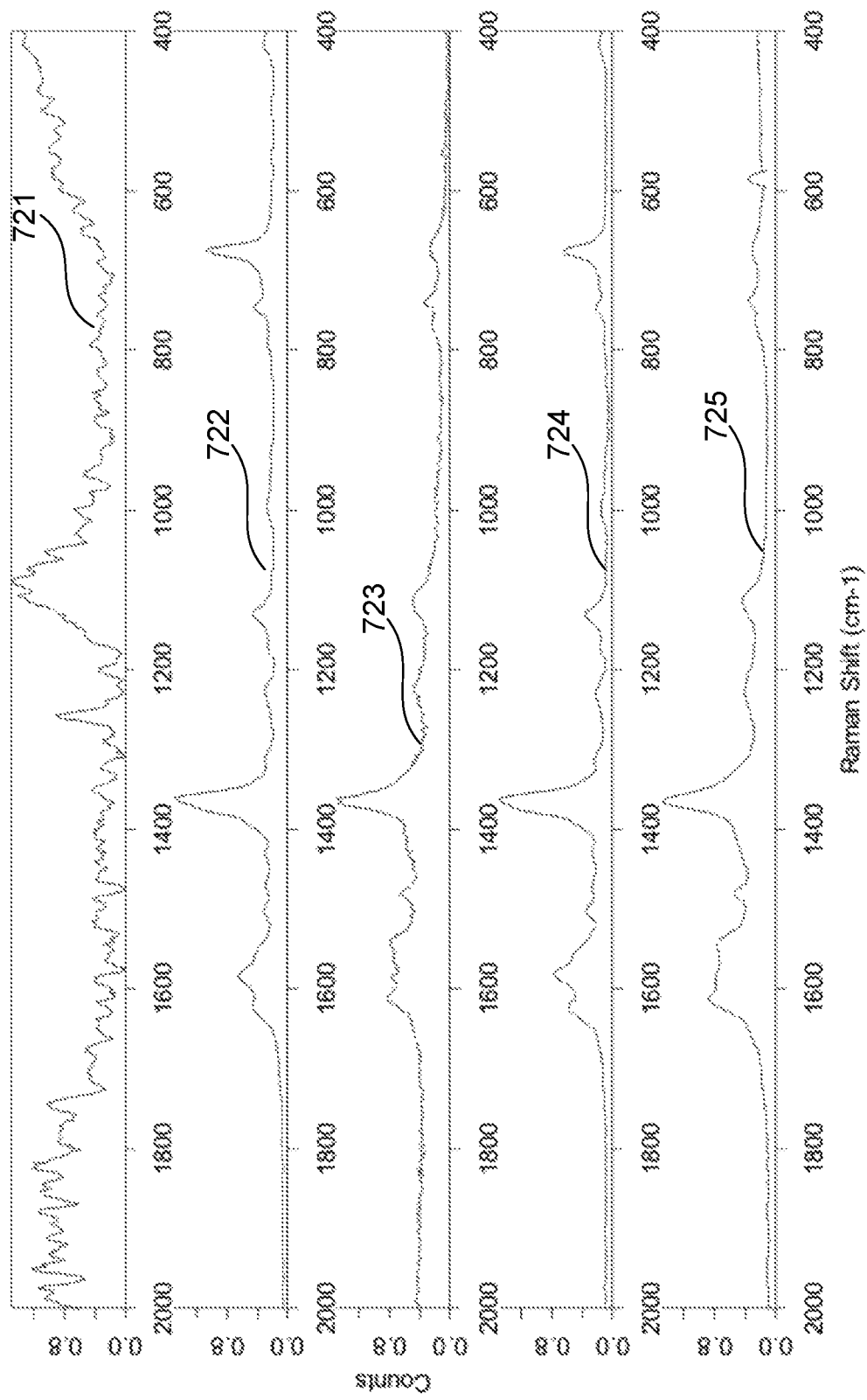
FIG. 7B is a trace of an example of Raman signals from stable plaque section without autofluorescence in comparison with Raman signals from purified haeme, methaeme and protoporphrin 1X compounds.
Figure 7D:
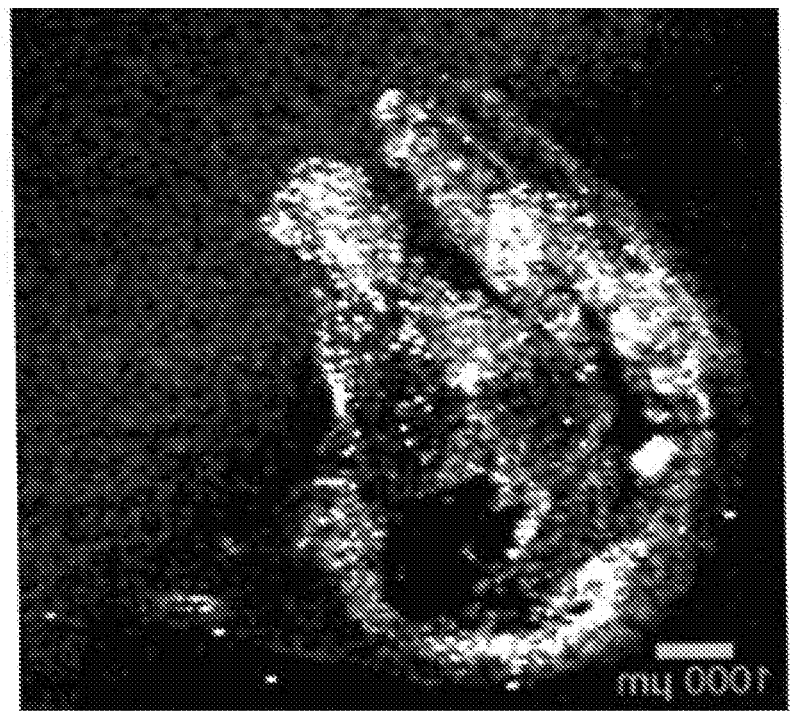
FIG. 7D is an image of an example of autofluorescence of the intraplaque haemorrhages of FIG. 7C.
Figure 7C:
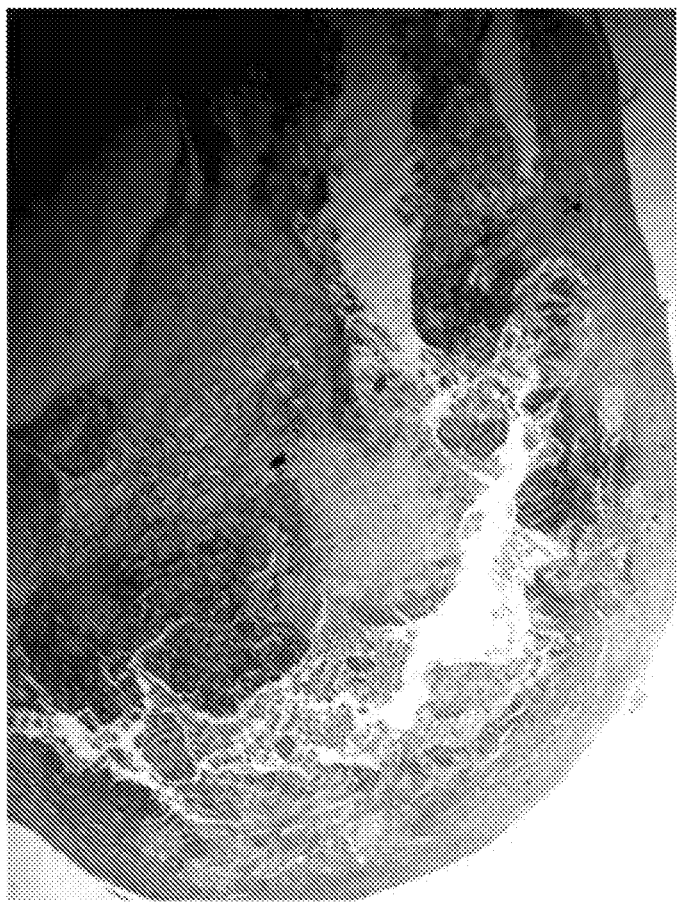
FIG. 7C is an image of an example of trichrome staining of intraplaque haemorrhages in the plaque.

| Healthy sample # | Autofluorescence intensity units | Unstable sample # | Autofluorescence intensity units | Fold change |
|---|---|---|---|---|
| 1 | 10 | 1 | 260 | 26 |
| 2 | 4 | 2 | 64 | 16 |
| 3 | 1 | 3 | 10 | 10 |
| 4 | 2 | 4 | 42 | 21 |
| 5 | 28 | 5 | 203 | 7.25 |
| 6 | 5 | 6 | 100 | 20 |
| 7 | 10 | 7 | 198 | 19.8 |
| 8 | 30 | 8 | 120 | 4 |
| 9 | 2 | 9 | 34 | 17 |
| 10 | 10 | 10 | 33 | 3.3 |
| 11 | 5 | 11 | 16 | 3.2 |
| 12 | 10 | 12 | 64 | 6.4 |
| 13 | 4 | 13 | 15 | 3.75 |
| 14 | 6 | 14 | 32 | 5.3 |
| 15 | 11 | 15 | 59 | 5.36 |
| 16 | 5 | 16 | 15 | 3 |
| 17 | 5 | 17 | 17 | 3.4 |
| 18 | 7 | 18 | 103 | 14.71 |
| 19 | 8 | 19 | 29 | 3.62 |
| 20 | 9 | 20 | 41 | 4.56 |
| Mean +/− SD | 8.6 +/− 7.6 | Mean +/− SD | 72.75 +/− 71.6 | 9.88 +/− 7.5 | signals from purified haeme 714, met-haeme 712 and two examples of Raman signals of the same sample of protoporphrin IX compounds 713, 715. FIG. 7B is an example of Raman signals from stable plaque section without autofluorescence 721 in comparison with Raman signals from purified haeme 724, met-haeme 722 and two examples of Raman signals of the same sample of protoporphrin IX compounds 723, 725. FIG. 7C shows an example of a trichrome staining image of an "intraplaque haemorrhages in the plaque", and FIG. 7D shows an autofluorescence image of the "intraplaque haemorrhages in the plaque" of the example in FIG. 7C.

It will be appreciated that given the above, it would be considered routine for a person skilled in the art to further characterise the optimal exposure and sensing wavelengths, or first and second wavelengths, of these molecular species.

Accordingly, the above-described method uses an autofluorescence property of vulnerable atherosclerotic plaques in NIR range without the use of any external fluorochromes. NIR spectroscopy has a number of advantages over other detection techniques allowing for the detection of vulnerable atherosclerotic plaques in the arteries such as coronary arteries and carotid arteries.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art, should be considered to fall within the spirit and scope that the invention broadly appearing before described.

What is claimed is:

1. A method for detecting autofluorescence from biological tissue for diagnosing the presence, absence or degree of vulnerability of an atherosclerotic plaque, the method comprising:
    a) measuring an at risk level of intensity of autofluorescence, the measuring of the at risk level of intensity of autofluorescence, comprising:
        1) exposing an at risk part of an artery to radiation at a first infrared wavelength using a radiation source, the at risk part being an area at risk of having a vulnerable atherosclerotic plaque;
        2) emitting a second infrared wavelength by autofluorescence from the exposed at risk part of the artery; and
        3) sensing the intensity of fluorescence emitted at the second wavelength by a sensor;
    b) measuring a healthy level of intensity of autofluorescence, the measuring of the healthy level of intensity of autofluorescence, comprising:
        1) exposing a healthy part of an artery to radiation at the first infrared wavelength using the radiation source;
        2) emitting the second infrared wavelength by autofluorescence from the exposed healthy part of the artery; and
        3) sensing the intensity of fluorescence emitted at the second wavelength by the sensor; and,
    c) calculating a fluorescence indicator based on the first level of intensity of fluorescence and the second level of intensity of fluorescence by:
        1) comparing the at risk level of intensity of autofluorescence to the healthy level of intensity of autofluorescence to determine if the at risk level of intensity of autofluorescence is more than twice the healthy level of intensity of autofluorescence; and,
        2) determining the fluorescence indicator based on the results of the comparison,
    wherein:
        the first wavelength is in the range 650 nm to 800 nm;
        the second wavelength is in the range 700 nm to 850 nm; and
        the second wavelength is longer than the first wavelength, and
    diagnosing the presence, absence or degree of vulnerability of an atherosclerotic plaque using the fluorescence indicator.

2. The method according to claim 1, wherein the radiation source includes a laser.

3. The method according to claim 1, wherein the sensor includes an infrared photodetector.

4. The method according to claim 1, wherein an apparatus for performing the method comprises optics for focusing radiation.

5. The method according to claim 1, wherein an apparatus for performing the method comprises a catheter including one or more optical fibers extending between proximal and distal ends, the distal end being for insertion into an artery, and the radiation source and sensing device being coupled to the proximal end.

6. The method according to claim 1, wherein an apparatus for performing the method comprises a bandpass filter.

7. The method according to claim 1, wherein the first wavelength is at least one of:
    a) 685 nm; and
    b) 785 nm.

8. The method according to claim 1, wherein the second wavelength is at least one of:
    a) 700 nm; and
    b) 800 nm.

9. The method according to claim 1, wherein the apparatus is configured to provide representation comprising at least one of:
    a) a numerical value indicative of the fluorescence indicator;
    b) a symbolic value indicative of the fluorescence indicator;
    c) a graphical indicator indicative of the fluorescence indicator; and,
    d) an indicator of at least one threshold.

10. A method for detecting autofluorescence from biological tissue for diagnosing the presence, absence or degree of vulnerability of an atherosclerotic plaque, the method being performed using an apparatus comprising a catheter having one or more optical fibers extending between proximal and distal ends, the distal end being for insertion into an artery, and a laser and infrared photodetector being coupled to the proximal end, the method comprising:
    a) positioning the catheter in an artery;
    b) measuring an at risk level of intensity of autofluorescence, the measuring of the at risk level of intensity of autofluorescence, comprising:
        1) exposing an at risk part of the artery to radiation at a first infrared wavelength using a radiation source, the at risk part being an area at risk of having a vulnerable atherosclerotic plaque;
        2) emitting a second infrared wavelength by autofluorescence from the exposed at risk part of the artery; and 3) sensing the intensity of fluorescence emitted at the second wavelength by a sensor;
c) measuring a healthy level of intensity of autofluorescence, the measuring of the healthy level of intensity of autofluorescence, comprising:
 1) exposing a healthy part of an artery to radiation at the first infrared wavelength using the radiation source;
 2) emitting the second infrared wavelength by autofluorescence from the exposed healthy part of the artery; and
 3) sensing the intensity of fluorescence emitted at the second wavelength by the sensor; and,
d) calculating a fluorescence indicator based on the first level of intensity of fluorescence and the second level of intensity of fluorescence by:
 1) comparing the at risk level of intensity of autofluorescence to the healthy level of intensity of autofluorescence to determine if the at risk level of intensity of autofluorescence is more than twice the healthy level of intensity of autofluorescence; and,
 2) determining the fluorescence indicator based on the results of the comparison,
wherein:
 the first wavelength is in the range 650 nm to 800 nm;
 the second wavelength is in the range 700 nm to 850 nm; and
 the second wavelength is longer than the first wavelength, and
diagnosing the presence, absence or degree of vulnerability of an atherosclerotic plaque using the fluorescence indicator.

11. A method for detecting autofluorescence from biological tissue for diagnosing the presence, absence or degree of vulnerability of an atherosclerotic plaque, the method comprising:
a) measuring an at risk level of intensity of autofluorescence, the measuring of the at risk level of intensity of autofluorescence, comprising:
 1) exposing an at risk part of the artery to radiation at a first infrared wavelength using a radiation source, the at risk part being an area at risk of having a vulnerable atherosclerotic plaque;
 2) emitting a second infrared wavelength by autofluorescence from the exposed at risk part of the artery; and
 3) sensing the intensity of fluorescence emitted at the second wavelength by a sensor;
b) measuring by the sensor a healthy level of intensity of autofluorescence, the measuring of the healthy level of intensity of autofluorescence, comprising:
 1) exposing a healthy part of an artery to radiation from the radiation source at the first infrared wavelength using the radiation source;
 2) emitting the second infrared wavelength by autofluorescence from the exposed healthy part of the artery; and
 3) sensing the intensity of fluorescence emitted at the second wavelength by the sensor;
c) calculating a fluorescence indicator based on the first level of intensity of fluorescence and the second level of intensity of fluorescence by:
 1) comparing the at risk level of intensity of autofluorescence to the healthy level of intensity of autofluorescence to determine if the at risk level of intensity of autofluorescence is more than twice the healthy level of intensity of autofluorescence; and,
 2) determining the fluorescence indicator based on the results of the comparison,
wherein:
 the first wavelength is in the range 650 nm to 800 nm;
 the second wavelength is in the range 700 nm to 850 nm; and
 the second wavelength is longer than the first wavelength; and,
d) displaying a representation comprising at least one of:
 a) a numerical value indicative of the fluorescence indicator;
 b) a symbolic value indicative of the fluorescence indicator; and,
 c) a graphical indicator indicative of the fluorescence indicator, and
diagnosing the presence, absence or degree of vulnerability of an atherosclerotic plaque using the fluorescence indicator.

* * * * *

UNITED STATES PATENT AND TRADEMARK OFFICE
CERTIFICATE OF CORRECTION

PATENT NO. : 10,835,127 B2
APPLICATION NO. : 14/394057
DATED : November 17, 2020
INVENTOR(S) : Karlheinz Peter It is certified that error appears in the above-identified patent and that said Letters Patent is hereby corrected as shown below:

On the Title Page

Column 1, item (72), Line 2, under Inventors, delete "Yara" and insert --Yarra--.

Page 2, Column 2, item (56), Line 4, under Other Publications, delete "Noninvasice" and insert --NonInvasive--.

Page 2, Column 2, item (56), Line 5, under Other Publications, delete "Autofluroescence" and insert --Autofluorescence--.

In the Drawings

Figure 2:
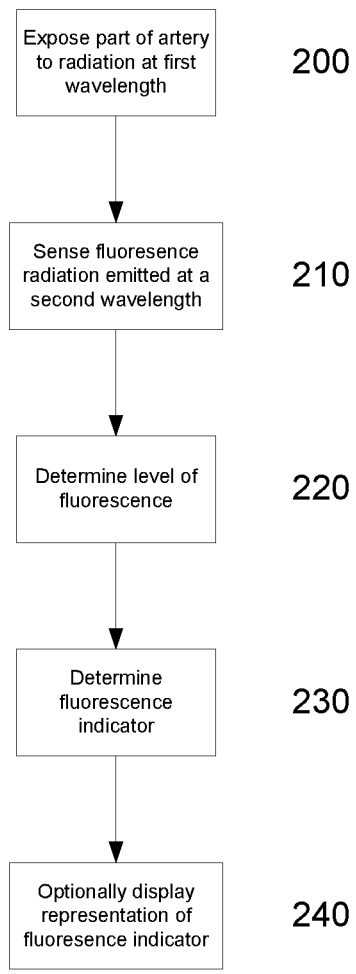
FIG. 2 is a flowchart of an example of a process for use in detecting atherosclerotic plaques.

Sheet 3 of 11, FIG. 2, Reference Number 210, Line 1, delete "fluoresence" and insert --fluorescence--.

Sheet 3 of 11, FIG. 2, Reference Number 240, Line 3, delete "fluoresence" and insert --fluorescence--.

Figure 3:
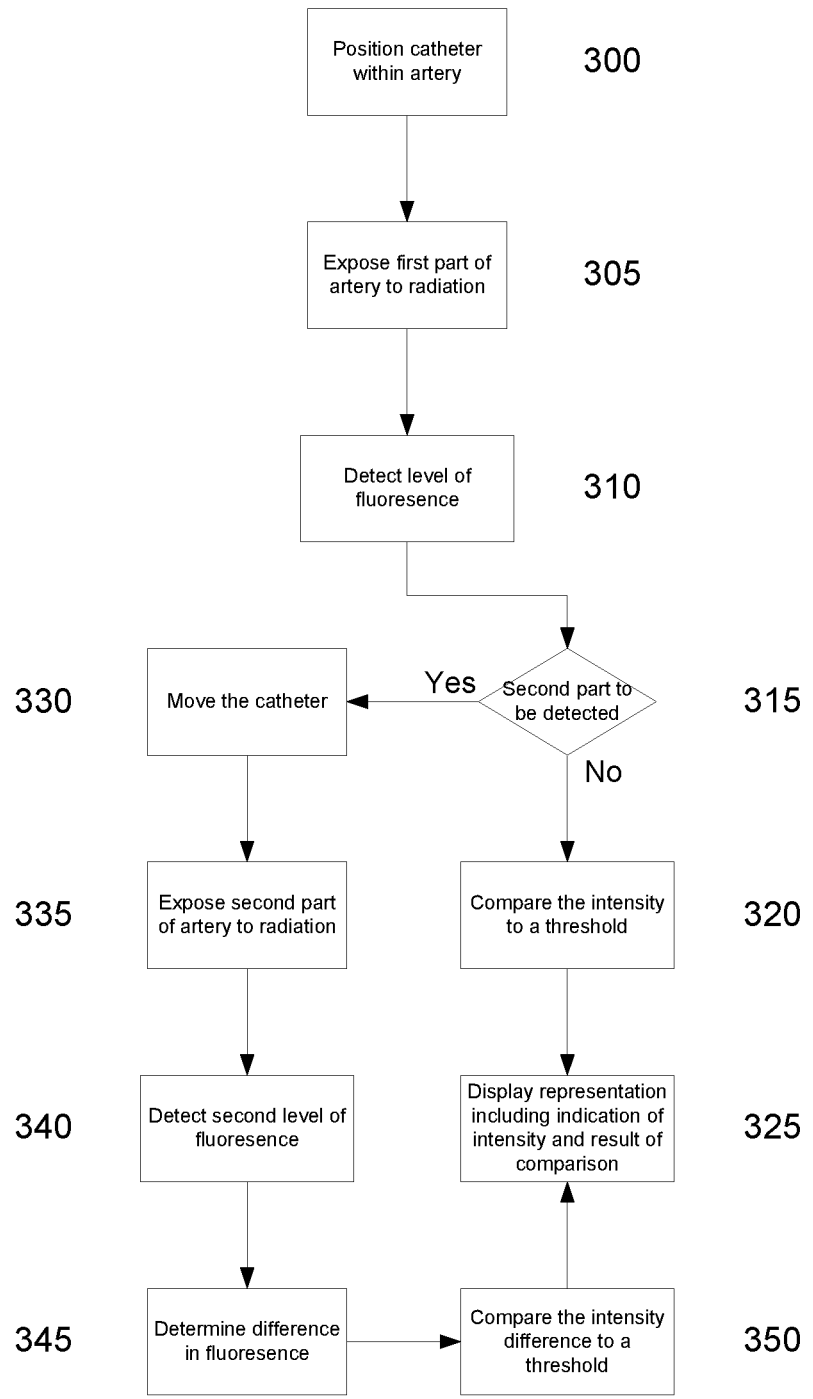
FIG. 3 is a flowchart of a second example of a process for use in detecting atherosclerotic plaques.

Sheet 4 of 11, FIG. 3, Reference Number 310, Line 2, delete "fluoresence" and insert --fluorescence--.

Sheet 4 of 11, FIG. 3, Reference Number 340, Line 2, delete "fluoresence" and insert --fluorescence--.

Sheet 4 of 11, FIG. 3, Reference Number 345, Line 2, delete "fluoresence" and insert --fluorescence--.

Sheet 8 of 11, FIG. 6A, Line 1, delete "Ramen" and insert --Raman--.

In the Specification

Column 2, Line 51, delete "WO2005/052558" and insert --WO 2005/052558--.

Column 2, Line 63, delete "SUMMARY OF THE PRESENT INVENTION" and insert --SUMMARY--.

Signed and Sealed this
Ninth Day of November, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,835,127 B2

Column 3, Line 54, delete "and" and insert --and,--.

Column 6, Line 14, delete "(right)" and insert --(right);--.

Column 6, Line 18, delete "protoporphrin" and insert --protoporphyrin--.

Column 6, Line 22, delete "protoporphrin 1X" and insert --protoporphyrin IX--.

Column 7, Line 6, delete "farther" and insert --further--.

Column 7, Line 44, delete "the" and insert --be--.

Column 9, Line 8, delete "PIM" and insert --PDA--.

Column 10, Lines 54-55, delete "950 nm 1150 nm," and insert --950 nm-1150 nm,--.

Column 10, Line 56, delete "750 nm 1100 nm," and insert --750 nm-1100 nm,--.

Column 10, Line 63, delete "750 nm 950 nm," and insert --750 nm-950 nm,--.

Column 13, Line 50, delete "the or" and insert --the--.

Column 14, Line 9, delete "IIb/IIIc" and insert --IIb/IIIa--.

Column 14, Line 10, delete "LIES" and insert --LIBS--.

Column 14, Line 11, delete "microparticles of iron oxide (MIPO)," and insert --microparticles of iron oxide (MPIO),--.

Column 14, Line 12, delete "LIRSs" and insert --LIBSs--.

Column 16, Line 26, delete "protopozphyrin" and insert --protoporphyrin--.

Column 17, Lines 2-3, delete "protoporphrin" and insert --protoporphyrin--.

Column 17, Line 7, delete "protoporphrin" and insert --protoporphyrin--.